(12) United States Patent
Strand et al.

(10) Patent No.: US 10,973,746 B2
(45) Date of Patent: *Apr. 13, 2021

(54) ORAL CARE COMPOSITIONS FOR PROMOTING GUM HEALTH

(71) Applicant: The Procter & Gamble Company, Cincinnati, OH (US)

(72) Inventors: Ross Strand, Singapore (SG); Yunming Shi, Beijing (CN)

(73) Assignee: The Procter & Gamble Company, Cincinnati, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/026,746

(22) Filed: Sep. 21, 2020

(65) Prior Publication Data

US 2021/0000723 A1   Jan. 7, 2021

Related U.S. Application Data

(63) Continuation of application No. 16/743,014, filed on Jan. 15, 2020, now Pat. No. 10,813,864, which is a continuation of application No. 16/369,658, filed on Sep. 16, 2019, now Pat. No. 10,603,263.

(30) Foreign Application Priority Data

Mar. 29, 2018 (WO) .............. PCT/CN2018/081109

(51) Int. Cl.
| | | |
|---|---|---|
| A61K 8/44 | (2006.01) | |
| A61K 8/21 | (2006.01) | |
| A61K 8/25 | (2006.01) | |
| A61K 8/34 | (2006.01) | |
| A61C 11/00 | (2006.01) | |
| A61Q 11/00 | (2006.01) | |

(52) U.S. Cl.
CPC .............. *A61K 8/442* (2013.01); *A61C 11/00* (2013.01); *A61K 8/21* (2013.01); *A61K 8/25* (2013.01); *A61K 8/345* (2013.01); *A61Q 11/00* (2013.01); *A61K 2800/28* (2013.01); *A61K 2800/30* (2013.01); *A61K 2800/48* (2013.01); *A61K 2800/592* (2013.01)

(58) Field of Classification Search
CPC .................................. A61K 8/25; A61K 8/44
See application file for complete search history.

(56) References Cited

U.S. PATENT DOCUMENTS

| | | | |
|---|---|---|---|
| 4,363,794 A | 12/1982 | Ochiai | |
| 4,902,497 A | 2/1990 | Crisanti | |
| 5,281,410 A | 1/1994 | Lukacovic | |
| 6,607,711 B2 | 8/2003 | Pedersen | |
| 6,846,478 B1 | 1/2005 | Doyle | |
| 8,283,135 B2 | 10/2012 | Doyle | |
| 8,652,495 B2 | 2/2014 | Porter | |
| 8,691,190 B2 | 4/2014 | Haught | |
| 9,532,932 B2 | 1/2017 | Prencipe | |
| 9,883,995 B2 | 2/2018 | Prencipe | |
| 10,105,303 B2 | 10/2018 | Pan | |
| 10,603,263 B2 | 3/2020 | Strand | |
| 2003/0157145 A1 | 8/2003 | Kalili | |
| 2009/0186090 A1 | 7/2009 | Zaidel | |
| 2009/0202450 A1 | 8/2009 | Prencipe | |
| 2009/0202451 A1 | 8/2009 | Prencipe | |
| 2010/0322987 A1 | 12/2010 | Robinson | |
| 2010/0322988 A1 | 12/2010 | Prencipe | |
| 2010/0330003 A1 | 12/2010 | Robinson | |
| 2011/0052509 A1 | 3/2011 | Subramanyam | |
| 2013/0142736 A1 | 6/2013 | Robinson | |
| 2015/0297477 A1 | 10/2015 | Poth | |
| 2015/0297500 A1 | 10/2015 | Robinson | |
| 2015/0313813 A1 | 11/2015 | Rege | |
| 2017/0020801 A1 | 1/2017 | Santarpia | |
| 2017/0056531 A1 | 3/2017 | Shi | |
| 2017/0100312 A1 | 4/2017 | Prencipe | |
| 2017/0319444 A1 | 11/2017 | Dehghan | |
| 2017/0319447 A1 | 11/2017 | Vemishetti | |
| 2017/0348206 A1 | 12/2017 | Vemishetti | |
| 2017/0348550 A1 | 12/2017 | Josias | |
| 2018/0072944 A1 | 3/2018 | Shi | |
| 2018/0147125 A1 | 5/2018 | Vemishetti | |
| 2019/0298620 A1 | 10/2019 | Strand | |
| 2019/0298634 A1 | 10/2019 | Strand | |
| 2019/0298635 A1 | 10/2019 | Strand | |

FOREIGN PATENT DOCUMENTS

| | | |
|---|---|---|
| CN | 20110133194 A | 6/2010 |
| CN | 106075545 A | 6/2016 |
| EP | 0311260 B1 | 12/1994 |
| EP | 0740932 B1 | 9/2002 |
| EP | 1203575 B1 | 9/2010 |
| EP | 1843741 B1 | 4/2013 |
| EP | 2753292 B1 | 6/2018 |
| JP | 6366113 | 3/1988 |
| JP | 02184617 A | 7/1990 |

(Continued)

OTHER PUBLICATIONS

PCT Search Report and Written Opinion for PCT/CN2018/081054 dated Mar. 29, 2018.
Supplemental PCT Search Report for PCT/CN2018/081054 dated Mar. 29, 2018.
PCT Search Report and Written Opinion.
Supplemental PCT Search Report for PCT/CN2018/081104 dated Mar. 29, 2018.
PCT Search Report and Written Opinion for PCT/CN2018/081107 dated Mar. 29, 2018.

(Continued)

*Primary Examiner* — Benjamin J Packard
(74) *Attorney, Agent, or Firm* — Parker D. McCrary

(57) ABSTRACT

Oral care compositions comprising an amino acid and stannous ion source, especially in the absence of zinc ion source, are provided for promoting Gum Health of a user.

24 Claims, 2 Drawing Sheets

(56) References Cited

FOREIGN PATENT DOCUMENTS

| WO | 2016178652 A1 | 11/2016 |
|----|---------------|---------|
| WO | 2017223169 A1 | 12/2017 |
| WO | 2018118138 A1 | 6/2018  |

OTHER PUBLICATIONS

PCT_Supplemental_SearchReport for PCT/CN2018/081107 dated Jun. 6, 2020.
Supplemental PCT Search Report for PCT/CN2018/081109 filed Mar. 29, 2018.
PCT Search Report and Written Opinion for PCT/CN2018/081109 dated Mar. 29, 2018.
http://www.colgatetotal.com/total-benefits/whole-mouth-health/gingivitis-control.
Xiang J, Li H, Pan B, Chang J, He Y, He T, Strand R, Shi Y, Dong W. (2018) Penetration and Bactericidal Efficacy of Two Oral Care Products in an Oral Biofilm Model. Am J Dent, vol. 31, Issue 1: 53-60.
All Office Actions for U.S. Appl. No. 16/369,658, filed Mar. 29, 2019.
All Office Actions for U.S. Appl. No. 16/743,014, filed Jan. 15, 2020.

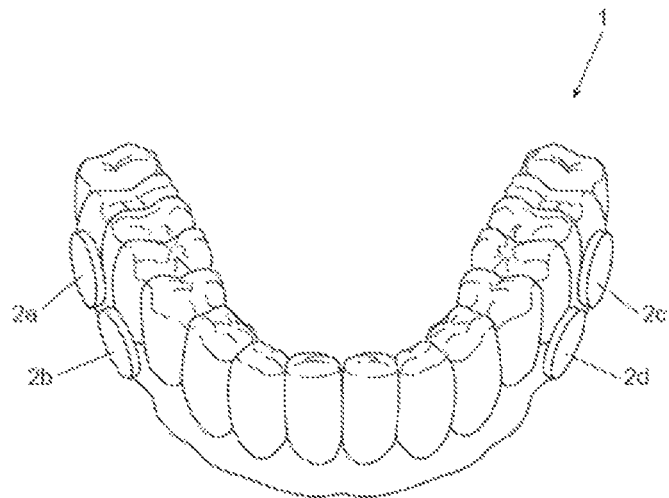
Figure 1 – Oral Splint with HA Disks
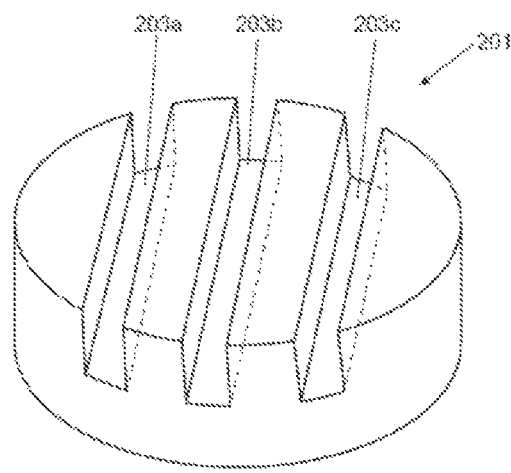
Figure 2 – HA Disk having Grooves

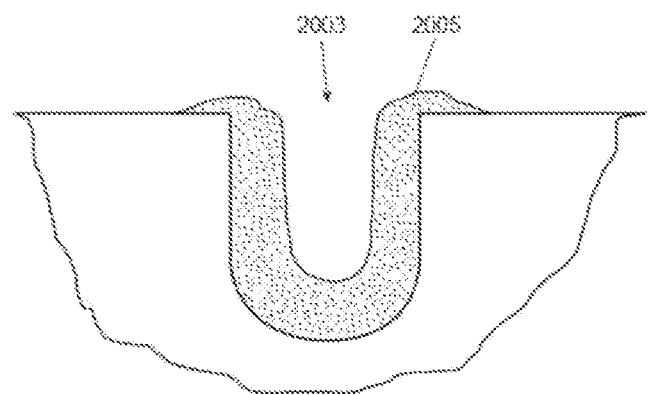
Figure 3 – Cross-Sectional View of the Grooves

ORAL CARE COMPOSITIONS FOR PROMOTING GUM HEALTH

FIELD OF THE INVENTION

The present invention relates to oral care compositions comprising stannous ion source and an amino acid with absence of zinc ion source for promoting Gum Health of a user. In particular, such oral care compositions are useful for improving gingival wound healing and improving the reduction of bacterial activity in the oral cavity of the user.

BACKGROUND OF THE INVENTION

Gum disease, such as gingivitis and/or periodontitis, gives rise to acute and chronic gum inflammation in the oral cavity. "Gingivitis" is the milder form of the disease. Symptoms of gingivitis may include: gingival bleeding; and redness, swollen, or tender gums. If left untreated, gingivitis can advance to "periodontitis". With periodontitis, gums pull away from the teeth and form spaces called "periodontal pockets" that can become infected by pathogenic bacteria. The bacteria are present on the tooth root surfaces as biofilms. The bacteria in the biofilms can attack the gingival and underlying alveolar bone supporting teeth. These attacks can cause major damage to the soft tissue and bone that support teeth. In the later stage of gum disease (i.e., "advanced periodontitis"), more serious problems of loosening of teeth and eventual tooth loss can occur.

Some commercially available oral care compositions aim, principally, at alleviating one or more symptoms of the earlier stage of gum disease (i.e., gingivitis), which includes: relief of red, swollen, or tender gums; and/or stem gum bleeding. Typically, these compositions claim benefits such as, "gum care", "oral care", "oral health", "dental care," or "dental health" to users. An example of such a composition is "Colgate® Total" toothpaste, which they claim to "help reduce the first stage of gum disease", which is defined as "gingivitis, or bleeding gums" (see http://www.colgatetotal-.com/total-benefits/whole-mouth-health/gingivitis-control). To help distinguish the benefits of the commercially available oral care compositions versus the present invention, the inventors herein refer to the aforementioned benefits of these commercially available oral care compositions collectively as "Gum Care". This is because these commercially available oral care compositions have been formulated primarily to care for the gums and relieve the symptoms (e.g., gum bleeding; and/or redness, swelling, or tender gums) associated with the earlier stage of gum disease (i.e., gingivitis).

However, there is a need to provide overall "Gum Health" benefits, which as used herein, is a broader term and is intended to encompass at least some of the aforementioned Gum Care benefits, as well as providing additional anti-bacterial benefits to mitigate the harmful effects of bacteria as it relates to gum disease, including gingivitis, periodontitis, or both.

There is at least one of several drawbacks to the above described conventional approaches. Firstly, these commercially available oral care compositions may promote Gum Care, but they do not go far enough to also promote Gum Health. In fact, these commercially available oral care compositions generally fail to provide any significant anti-bacterial effects in addition to the Gum Care benefits (e.g., anti-bleeding and/or anti-swelling). This is a problem because if the bacteria in the biofilms are not controlled, they can then increase the size of the periodontal pockets leading to periodontitis. Secondly, Gum Health may correlate to overall body health. In other words, an individual's Gum Health can be an indicator of the person's overall body health. Studies suggest that the risk of developing any one (or more) of these potential life-threatening conditions such as, for example, heart disease and stroke, diabetes, kidney disease, preterm birth, and/or osteoporosis, may increase as overall Gum Health decreases (see U.S. Pat. No. 6,846,478; Doyle, M. J.; & U.S. Pat. No. 8,283,135; Doyle, M. J.). Thus, it is desirable to improve overall Gum Health, not just Gum Care, in order to ensure better overall body health.

Stannous salts, such as stannous fluoride has been used in oral care compositions as to provide Gum Health benefit, including antimicrobial effect, reduced gingivitis, decreasing progression to periodontal disease, reductions in dentinal hypersensitivity, and reduced coronal and root dental caries and erosion. However, there are disadvantages for conventional stannous containing compositions. A first side effect routinely encountered during use of effective stannous fluoride formulations is unacceptable formulation astringency. secondly, formulating stannous ions stably also presents a challenge as the tin (II) ion is both prone to oxidation towards tin (IV) and to precipitate from aqueous solution as stannous hydroxide. Thirdly, stannous salts tend to discolor the oral care compositions, turning them yellow to dark brown. In order to overcome this problem, those conventional stannous containing compositions further comprising additional components such as, for example, $TiO_2$, folic acid or flavor mixtures (e.g., methyl salicylate, menthol, eugenol and cineol) to prevent the above-described discoloration in storage without significantly diminishing the stability and activity of stannous salts. Therefore, it is desired to simplify formulations and processing steps to provide cost effective and efficacious toothpaste and other oral care formulations.

Oral care compositions containing stannous salts and zinc ion source have been described. Soluble zinc salts, such as zinc citrate, have been used in dentifrice compositions, but have several disadvantages. Free zinc ions may react with fluoride ions to produce zinc fluoride, which is insoluble and so reduces the availability of both the zinc and the fluoride. Moreover, zinc ions in solution impart an unpleasant, astringent mouthfeel, so formulations that provide effective levels of zinc, and also have acceptable organoleptic properties, have been difficult to achieve. Finally, the zinc ions will react with anionic surfactants such as sodium lauryl sulfate, thus interfering with foaming and cleaning. Therefore, there is a need to optimize the usage of zinc in the formulation.

Therefore, there is a continuous need to provide an oral care composition that provides Gum Health benefits to users, or at least provide better associated Gum Health benefits (e.g., gingival wound healing and anti-bacterial benefits) than those compositions that are commercially available.

SUMMARY OF THE INVENTION

The present invention attempts to address this need based, at least in part, on the surprising discovery that the combination of an amino acid and a stannous ion source in absence of zinc ion source in an oral care composition promotes Gum Health benefits that include at least gingival wound healing and anti-bacterial benefits. In particular, the oral care composition comprises amino acid for gingival wound healing, and stannous ion source as an anti-bacterial agent without the presence of zinc ion source to combat the undesirable effects of bacteria activity in the oral cavity.

One advantage of the present invention is "better deep biofilm penetration and/or bacteria kill". To this end, it is further surprisingly found that the penetration depth and/or penetration rate of stannous ion into the biofilms may be increased, when used in combination with amino acid, especially in absence of zinc ion. In short, the synergistic combination of amino acid and stannous ion source without presence of zinc ion source in the oral care composition may be such that an improvement in the Gum Health benefit is achieved. Furthermore, the use of the oral care compositions of the present invention may provide the users an improved Gum Health benefit.

Another advantage of the present invention is to provide oral care compositions for promoting Gum Health as it relates to the totality of symptoms associated with gingivitis, periodontitis, or both. It is yet a further advantage that the oral care compositions of the present invention have improved Gum Health benefits. It is yet a further advantage of the present invention to provide oral care compositions having improved penetration depth of the anti-bacterial agent(s) into the biofilms. It is yet a further advantage of the present invention to provide oral care compositions having improved penetration rate of the anti-bacterial agent(s) into the biofilms. It is yet a further advantage of the present invention to provide cost effective and efficacious oral care compositions for promoting Gum Health. It is yet a further advantage that the oral care composition, is a dentifrice, and preferably provides pleasant taste and mouth-feel experience. It is yet a further advantage that the oral care compositions have physical and chemical stability across a range of manufacturing, handling and storage conditions. It is yet a further advantage that the oral care compositions have a stable quality of end product (e.g., consistent visual appearance and no discoloration, gingival wound healing performance, etc.) even after three months storage at 40° C. It is yet a still further advantage that the oral care compositions of the present invention minimize the use of anti-bacterial agents. It is yet a still further advantage that the oral compositions of the present invention minimize the amount of the amino acid to reduce and/or eliminate the instability and/or discoloration problems as described above.

In one aspect, the present invention is directed to an oral care composition, comprising: (a) from 0.01% to 5%, by weight of the composition, of a stannous ion source; and (b) from 0.01% to 10%, by weight of the composition, of an amino acid in free or salt form; wherein the oral care composition is substantially free of zinc ion source. Preferably, the oral care composition is essentially free of zinc ion source. More preferably, the oral care composition is free of zinc ion source.

Preferably, the amino acid used in the present invention is selected from the group consisting of arginine, lysine, citrulline, ornithine, creatine, histidine, diaminobutanoic acid, diaminoproprionic acid, aspartic acid, glutamic acid, glycine, asparagine, glutamine and combinations thereof; preferably the amino acid is present in the amount of 0.1% to 5%, more preferably from 0.3% to 3%, by weight of the composition. The amino acid can be in their free form or salts form.

In yet still another aspect of the present invention, a method is provided for promoting Gum Health in a human subject comprising administering to the subject's oral cavity an oral care composition of the present invention.

These and other features of the present invention will become apparent to one skilled in the art upon review of the following detailed description when taken in conjunction with the appended claims.

BRIEF DESCRIPTION OF THE DRAWINGS

While the specification concludes with claims that particularly point out and distinctly claim the invention, it is believed the present invention will be better understood from the following description of the accompanying figures.

FIG. 1 is a perspective view of an oral splint with Hydroxyapatite ("HA") disks attached thereto.

FIG. 2 is a perspective view of the HA disk having grooves therein.

FIG. 3 is a schematic of a cross sectional view of the groove with biofilm therein.

DETAILED DESCRIPTION OF THE INVENTION

Definitions

As used herein, the articles including "a" and "an" when used in a claim, are understood to mean one or more of what is claimed or described.

The terms "alleviate" and "alleviating" are used interchangeably and means minimizing, preventing, delaying, and/or treating at least one symptom of gum disease to effect positive change (i.e., benefit) to the user.

The term "biofilms" as used herein means a matrix-enclosed bacterial population adherent to each other and/or to surfaces or interfaces in the oral cavity.

The term "comprising" as used herein means that steps and ingredients other than those specifically mentioned can be added. This term encompasses the terms "consisting of" and "consisting essentially of." The compositions of the present invention can comprise, consist of, and consist essentially of the essential elements and limitations of the invention described herein, as well as any of the additional or optional ingredients, components, steps, or limitations described herein.

The term "dentifrice" as used herein means paste, gel, powder, tablets, or liquid formulations, unless otherwise specified, that are used to clean the surfaces of the oral cavity.

The term "Gum Care" as used herein refers to inherent or promoted benefits of an oral care composition directed, principally, to alleviating one or more symptoms associated with an early stage of gum disease (i.e., gingivitis). Such symptoms may include, for example bleeding gums; and red, swollen, or tender gums.

The term "Gum Health" as used herein refers to inherent or promoted benefits of an oral care composition to provide "Gum Care" benefits that include at least improve gingival wound healing, as well as, providing additional improve reduction of bacterial activity to mitigate the harmful effects of bacteria as it relates to gum disease, including gingivitis, periodontitis or both.

The term "improve reduction of bacterial activity" as used herein means reduce bacterial activity in the oral cavity as determined by the assay described in Example B.

The term "improve gingival wound healing" as used herein means reduce gum bleeding in the oral cavity as determined by the wound healing assay described in Example C.

The term "oral care composition" or "oral care compositions" as used herein means a product that in the ordinary course of usage is retained in the oral cavity for a time sufficient to contact some or all of the dental surfaces and/or oral tissues for purposes of oral activity. In one example, the composition provides a gum care benefit when used in the oral cavity. The oral care composition of the present invention may be in various forms including toothpaste, dentifrice, tooth gel, tooth powders, tablets, rinse, mouthwash, sub gingival gel, foam, mouse, chewing gum, lipstick, sponge, floss, prophy paste, petrolatum gel, denture adhesive, or denture product. In one example, the oral composition is in the form of a paste or gel. In another example, the oral composition is in the form of a dentifrice. The oral composition may also be incorporated onto strips or films for direct application or attachment to oral surfaces, or incorporated into floss.

The term "amino acid" used herein the present invention refers to the amino acid including both in free form and salts form.

The term "partially water soluble" as used herein means a compound has a solubility of 1 g/1000 ml or more at 25° C.

The term "effective amount" as used herein means an amount of a compound or composition sufficient to induce a positive benefit, an oral health benefit, and/or an amount low enough to avoid serious side effects, i.e., to provide a reasonable benefit to risk ratio, within the sound judgment of a skilled artisan. In one example, "effective amount" means at least 0.01% of the material, by weight of the composition, alternatively at least 0.1%.

As used herein, the words "preferred", "preferably" and variants refer to embodiments of the invention that afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

The term "promoting" as used herein means to promote and/or enhance the Gum Health benefits associated with using the oral care compositions of the present invention in the oral cavity.

The term "substantially free" as used herein refers to no intentional amount of that material is added to the composition or an amount of a material that is less than 0.05%, 0.01%, or 0.001% of the composition. The term "essentially free" as used herein means that the indicated material is not deliberately added to the composition, or preferably not present at analytically detectable levels. It is meant to include compositions whereby the indicated material is present only as an impurity of one of the other materials deliberately added. The term "free" as used herein refers to no reasonably detectable amount of that material is present in the composition.

The term "synergistic Gum Health benefit" as used herein means analytically measurable increases in any two Gum Health benefits that include at least improve gingival wound healing and improve reduction of bacterial activity in the oral cavity, that is more than additive.

The term "teeth" as used herein refers to natural teeth as well as artificial teeth or dental prosthesis.

The term "total water content" as used herein means both free water and water that is bound by other ingredients in the oral care composition.

All percentages, parts and ratios are based upon the total weight of the compositions of the present invention, unless otherwise specified. All such weights as they pertain to listed ingredients are based on the active level and, therefore do not include solvents or by-products that may be included in commercially available materials, unless otherwise specified.

All measurements referred to herein are made at 25° C. (i.e., room temperature) unless otherwise specified.

Oral Care Compositions

It has been surprisingly discovered that the combination of stannous ion (i.e., an anti-bacterial agent) and an amino acid, in the absence of zinc ion source, in an oral care composition is particularly useful for promoting Gum Health benefits to users. In particular, the surprising discovery was that the penetration of the stannous ion into the biofilms is markedly improved when combined with the amino acid. Without wishing to be bound by theory, the amino acid contains both carboxylic and amine groups. It is believed that the stannous ions can bind strongly to these chemical moieties on amino acid to positively influence the penetration of stannous ions into the biofilms.

It has also been surprisingly found that the penetration depth and/or the penetration rate of stannous ions into the biofilms may be increased, or markedly increased, when formulated with amino acid, especially without the presence of zinc. In short, the absence of zinc ion source and the presence of amino acid in combination with stannous ion source in an oral care composition aids the composition's efficacy in mediating the harmful effects of the bacteria in the biofilms on the gums.

In one aspect, the present invention is directed to an oral care composition comprising: a) from 0.01% to 5%, preferably from 0.05% to 4%, more preferably from 0.1% to 2%, by weight of the composition, of a stannous ion source; b) from 0.01% to 10%, preferably from 0.05% to 5%, more preferably from 0.1% to 2%, by weight of the composition, of an amino acid; and c) from 0% to 0.01%, by weight of the composition, of zinc ion source.

Stannous Ion Source

The present invention relates to the above mentioned oral care compositions comprising, in a preferred example, the stannous ion source present in the amount of from 0.01% to 5%, preferably from 0.05% to 4%, or more preferably from 0.1% to 2%, by weight of the composition, to provide anti-bacterial effectiveness. The stannous ion source used herein may include any safe and effective stannous salt. Suitable examples of stannous ion source are selected from the group consisting of stannous chloride, stannous fluoride, stannous acetate, stannous gluconate, stannous oxalate, stannous sulfate, stannous lactate, stannous tartrate, stannous iodide, stannous chlorofluoride, stannous hexafluorozirconate, stannous citrate, stannous malate, stannous glycinate, stannous carbonate, stannous phosphate, stannous pyrophosphate, stannous metaphosphate, and combinations thereof. Preferably, the stannous ion source is selected from stannous fluoride, stannous chloride, and combinations thereof. In one preferred example, the stannous ion source comprises stannous chloride. In another preferred example, the stannous ion source comprises stannous fluoride.

Amino Acids

The term "amino acids" as used herein include not only naturally occurring amino acids, but also any amino acids having an amino group and a carboxyl group in the molecule, which are water-soluble and pharmaceutically acceptable considered to be physiologically acceptable in the amounts and concentrations provided.

Suitable amino acids used in the present invention include, but not limited to, a basic amino acid such as arginine, lysine, serine, histidine, ornithine; a neutral amino acid such as alanine, aminobutyrate, asparagine, citrulline, cysteine, cystine, glutamine, glycine, hydroxyproline, isoleucine, leucine, methionine, phenylalanine, proline, serine, taurine, threonine, tryptophan, tyrosine, valine; or an acidic amino acid such as aspartic acid, glutamic acid; or combinations thereof. Each of said amino acids can be in its free form or in its salt form or a combination thereof. If the amino acid is in its salt form, suitable salts include salts known in the art to be pharmaceutically acceptable salts considered to be physiologically acceptable in the amounts and concentrations provided.

Preferably, the amino acids used in the present invention are selected from the group consisting of arginine, lysine, citrulline, asparagine, glutamine, glycine, aspartic acid, glutamic acid, and combinations thereof.

In some examples, the amino acid is selected from arginine, lysine, citrulline, in free form or salt form, or combinations thereof. In some examples, the amino acid is selected from asparagine, glutamine, or glycine, in free form or salt form, or combinations thereof. In some other examples, the amino acid is selected from aspartic acid, glutamic acid, in free form or salt form, or combinations thereof. If the amino acid is aspartic acid or glutamic acid in its salt form, non-limiting examples of such salts include those derived from alkali metals such as potassium and sodium or alkaline earth metals such as calcium and magnesium.

Preferably the amino acid is present in the amount of from 0.01% to 10%, from 0.05% to 5%, yet more preferably from 0.1% to 2%, alternatively from 0.2% to 3%, by weight of the composition.

Free of Zinc Ion Source

Preferably, the oral care compositions comprise from 0% to 0.01%, by weight of the composition, of a zinc ion source. Preferably, the zinc ion source is selected from zinc citrate, zinc chloride, zinc sulfate, zinc gluconate, zinc lactate, zinc phosphate, zinc oxide, zinc carbonate, and combinations thereof. More preferably, the zinc ion source is present in the amount of from 0% to less than 0.005%, or preferably from 0% to 0.001%, by weight of the composition; more preferably the oral care composition is free of zinc ion source.

Thickening Agent

The oral care compositions of the present invention may comprise a thickening agent. Preferably the oral care composition comprises from 0.1% to 5%, preferably from 0.8% to 3.5%, more preferably from 1% to 3%, yet still more preferably from 1.3% to 2.6%, by weight of the composition, of the thickening agent.

Preferably the thickening agent comprises a thickening polymer, a thickening silica, or a combination thereof. Yet more preferably, when the thickening agent comprises a thickening polymer, the thickening polymer is selected from a charged carboxymethyl cellulose, a non-ionic cellulose derivative, a linear sulfated polysaccharide, a natural gum, polymers comprising at least a polycarboxylated ethylene backbone, and combinations thereof.

In one example the thickening silica is obtained from sodium silicate solution by destabilizing with acid as to yield very fine particles. One commercially available example is ZEODENT® branded silicas from Huber Engineered Materials (e.g., ZEODENT® 103, 124, 113 115, 163, 165, 167).

Preferably the linear sulfated polysaccharide is a carrageenan (also known as carrageenin). Examples of carrageenan include Kappa-carrageenan, Iota-carrageenan, Lambda-carrageenan, and combinations thereof.

In one example the CMC is prepared from cellulose by treatment with alkali and monochloro-acetic acid or its sodium salt. Different varieties are commercially characterized by viscosity. One commercially available example is Aqualon™ branded CMC from Ashland Special Ingredients (e.g., Aqualon™ 7H3SF; Aqualon™ 9 M3SF Aqualon™ TM9A; Aqualon™ TM12A).

Preferably a natural gum is selected from the group consisting of gum karaya, gum arabic (also known as acacia gum), gum tragacanth, xanthan gum, and combination thereof. More preferably the natural gum is xanthan gum. Xanthan gum is a polysaccharide secreted by the bacterium *Xanthomonas camestris*. Generally, xanthan gum is composed of a pentasaccharide repeat units, comprising glucose, mannose, and glucuronic acid in a molar ratio of 2:2:1, respectively. The chemical formula (of the monomer) is $C_{35}H_{49}O_{29}$. In one example, the xanthan gum is from CP Kelco Inc (Okmulgee, US).

Preferably, the non-ionic cellulose or derivative thereof has an average molecular weight range of 50,000 to 1,300,000 Daltons, and preferably an average degree of polymerization from 300 to 4,800. More preferably, the non-ionic cellulose or derivative thereof is hydroxyethyl cellulose ("HEC").

Preferably the polymer comprising at least a polycarboxylated ethylene backbone is selected from the group consisting of: co-polymers of maleic anhydride with methyl vinyl ether having a molecular weight of 30,000 to 1,000,000 Daltons; homo-polymers of acrylic acid; and co-polymers of maleic acid and acrylic acid or methacrylic.

The co-polymers of maleic anhydride with methyl vinyl ether are at least one of: Gantrez AN139 (M.W. 500,000 daltons), Gantrez AN119 (M.W. 250,000 daltons), or S-97 Pharmaceutical Grade (M.W. 70,000 daltons); and the homo-polymers of acrylic acid and co-polymers of maleic acid and acrylic acid or methacrylic acid are at least one of: Acusol 445, Acusol 445N, Accusol 531, Acusol 463, Acusol 448, Acusol 460, Acusol 465, Acusol 490, Sokalan CPS, Sokalan CP7, Sokalan CP45, or Sokalan CP12S; and (v) combinations thereof.

In an example, the GANTREZ™ series of polymers are co-polymers of maleic anhydride with methyl vinyl ether having a molecular weight (M.W.) of 30,000 daltons to 1,000,000 daltons. These co-polymers are available for example as GANTREZ™ AN139 (M.W. 500,000 daltons), AN119 (M.W. 250,000 daltons) and S-97 Pharmaceutical Grade (M.W. 70,000 daltons), from Ashland Chemicals (Kentucky, USA).

In another example, the ACUSOL™ and the SOKALAN series of polymers include homopolymers of acrylic acid and copolymers of maleic acid and acrylic acid or methacrylic. Examples are 0:1000 to 1000:0 copolymers of maleic acid with acrylic acid having a molecular weight (M.W.) of about 2,000 to about 1,000,000. These copolymers are commercially available as ACUSOL™ 445 and 445N, ACUSOL™ 531, ACUSOL™ 463, ACUSOL™ 448, ACUSOL™ 460, ACUSOL™ 465, ACUSOL™ 497, ACUSOL™ 490 from Dow Chemicals (Michigan, USA) and as Sokalan® CP 5, Sokalan® CP 7, Sokalan® CP 45, and Sokalan® CP 12 S from BASF (New Jersey, USA).

In another example, the crosslinked polyacrylic acid (PAA) polymer is a generic term for the synthetic high molecular weight polymers of acrylic acid. These may be homopolymers of acrylic acid, crosslinked with an allyl ether pentaerythritol, allyl ether of sucrose or allyl ether of propylene. And, in a water solution at neutral pH, PAA is an anionic polymer, i.e. many of the side chains of PAA will lose their protons and acquire a negative charge. Carbopol®-type polymers, such as Carbopol®, Pemulen® and Noveon®, are polymers of acrylic acid, crosslinked with polyalkenyl ethers or divinyl glycol. Carbomer commercial codes, e.g. 940™, indicate the molecular weight and the specific components of the polymer.

Anti-Caries Agent

Optionally, but preferably, the oral care compositions may include an effective amount of an anti-caries agent. In one aspect, the anti-caries agent is a fluoride ion source. Suitable examples of fluoride ions may be selected from a source comprising stannous fluoride, sodium fluoride, potassium fluoride, sodium monofluorophosphate ("MFP"), indium fluoride, amine fluoride, zinc fluoride, and mixtures thereof. Preferably, the fluoride ion source is selected from sodium fluoride, stannous fluoride, MFP, or combinations thereof. The fluoride ion source may be present in an amount of from 0.0025% to 10%, or from 0.05% to 4%, or from 0.1% to 2%, or preferably from 0.2% to 1.5%, by weight of the composition, to provide anti-caries effectiveness. In certain examples, the fluoride ion source can be present in an amount sufficient to provide fluoride ions concentration in the composition at levels from 25 ppm to 25,000 ppm, generally at least from 500 ppm to 1600 ppm, for example 1100 ppm or 1450 ppm. The appropriate level of fluoride will depend on the particular application. A toothpaste for general user would typically have about 1000 to 1500 ppm, with pediatric toothpaste having somewhat less.

The pH of the oral care composition of the present invention may be from 4 to 11, preferably from pH 5 to 9, or more preferably from pH 5.0 to 7.2. Preferably, the pH is less than 7.2, more preferably the pH is 7.0 or less, even more preferably the pH is from pH 5.3 to pH 7.0, alternatively the pH is from pH 6.0 to less than pH 7.0, e.g., pH 6.9, or pH 6.8, or pH 6.7, or pH 6.6, or pH 6.5, or pH 6.4, or pH 6.3, or pH 6.2, or pH 6.2, or pH 6.1, or pH 6.0. The relatively low pH of the present inventive composition is for alleviating discoloration and optionally avoiding the precipitation of stannous. Without wishing to be bound theory, at above pH 7.3 stannous ion may increase the possibility of discoloration. Thus, it is desirable to have the oral care composition have a less than pH 7.0 to alleviate discoloration.

The pH is typically measured using a ratio of 1:3 of paste:water, whereby 1 gram of the oral care composition (e.g., toothpaste) is mixed into 3 grams of deionized water, and then the pH is assessed with an industry accepted pH probe that is calibrated under ambient conditions. The pH is measured by a pH meter with Automatic Temperature Compensating (ATC) probe. For purposes of clarification, although the analytical method describes testing the oral care composition when freshly prepared, for purposes of claiming the present invention, the pH may be taken at any time during the product's reasonable lifecycle (including but not limited to the time the product is purchased from a store and brought to the user's home).

After each usage the electrode should be washed free from the sample solution with water. Remove any excess water by wiping with a tissue, such as Kimwipes or equivalent. When electrode is not in use, keep electrode tip immersed in pH 7 buffer solution or electrode storage solution. Equipment details are as follows:

pH Meter: Meter capable of reading to 0.01 or 0.001 pH units.
Electrode: Orion Ross Sure-Flow combination: Glass body—VWR #34104-834/Orion #8172BN or VWR #10010-772/Orion #8172BNWP.
  Epoxy body—VWR #34104-830/Orion #8165BN or VWR #10010-770/Orion #8165BNWP.
  Semi-micro, epoxy body—VWR #34104-837/Orion #8175BN or VWR #10010-774/Orion #3175BNWP.
  Orion PerpHect combination: VWR #34104-843/Orion #8203BN semi-micro, glass body.
ATC Probe: Fisher Scientific, Cat. #13-620-16.

pH Modifying Agent

The oral care compositions herein may optionally include an effective amount of a pH modifying agent, alternatively wherein the pH modifying agent is a pH buffering agent. The pH modifying agents, as used herein, refer to agents that can be used to adjust the pH of the oral care compositions to the above-identified pH range. The pH modifying agents include hydrochloric acid, alkali metal hydroxides, ammonium hydroxide, organic ammonium compounds, carbonates, sesquicarbonates, borates, silicates, phosphates, imidazole, and mixtures thereof.

Specific pH modifying agents include monosodium phosphate (monobasic sodium phosphate), trisodium phosphate (sodium phosphate tribasic dodecahydrate or TSP), sodium benzoate, benzoic acid, sodium hydroxide, potassium hydroxide, alkali metal carbonate salts, sodium carbonate, imidazole, pyrophosphate salts, polyphosphate salts both linear and cyclic form, sodium gluconate, lactic acid, sodium lactate, citric acid, sodium citrate, phosphoric acid.

In one example, 0.01% to 3%, preferably from 0.1% to 1% of TSP by weight of the composition, and 0.001% to 2%, preferably from 0.01% to 0.3% of monosodium phosphate by weight of the composition is used. Without wishing to be bound by theory, TSP and monosodium phosphate may have calcium ion chelating activity and therefore provide some monofluorophosphate stabilization (in those formulations containing monofluorophosphate).

Water

Water is commonly used as a carrier material in oral care compositions due to its many benefits. For example, water is useful as a processing aid, is benign to the oral cavity and assists in quick foaming of toothpastes. Water may be added as an ingredient in its own right or it may be present as a carrier in other common raw materials such as, for example, sorbitol and sodium lauryl sulfate.

In some examples, the oral care compositions herein may include from 10% to 70%, or preferably from 15% to 30%, by weight of the composition, of total water content. The term "total water content" as used herein means the total amount of water present in the oral care composition, whether added separately or as a solvent or carrier for other raw materials but excluding that which may be present as water of crystallization in certain inorganic salts. Preferably, the water is USP water.

Alternatively, in other examples, the oral care compositions herein may include from 0% to 5%, by weight of the composition, of total water content. For example, the oral care composition may be substantially free of water, preferably free of water.

Surfactant

Optionally, but preferably, the oral care compositions comprise a surfactant. The surfactant may be selected from anionic, nonionic, amphoteric, zwitterionic, cationic surfactants, or combinations thereof, preferably the surfactant is anionic, more preferably the anionic surfactant is sodium lauryl sulfate (SLS). An example of a zwitterionic surfactant is cocamidopropyl betaine.

The oral care composition may contain one, two, or more surfactants. The composition may include a surfactant at a level of from 0.1% to 20%, preferably from 1% to 10%, by weight of the total composition.

Humectants

The oral care compositions herein may include humectants present in the amount of from 0% to 70%, or from 15% to 55%, by weight of the compositions. Humectants keep oral care compositions from hardening upon exposure to air and certain humectants may also impart desirable sweetness of flavor to oral care compositions. Suitable examples of humectants may include glycerin, sorbitol, polyethylene glycol, propylene glycol, xylitol, trimethyl glycine, and mixtures thereof. Other examples may include other edible polyhydric alcohols. In some examples, the humectant is selected from sorbitol, glycerin, and combinations thereof. Preferably the humectant is sorbitol. In an example, the composition comprises from 10% to 66%, alternatively from 30% to 55%, of humectant by weight of the composition.

Abrasives

The oral care compositions of the present invention comprise an effective amount of an abrasive. Examples of abrasives include a calcium-containing abrasive, a silica, or combinations thereof. If containing a calcium-containing abrasive, the calcium-containing abrasive is preferably selected from the group consisting of calcium carbonate, dicalcium phosphate, tricalcium phosphate, calcium orthophosphate, calcium metaphosphate, calcium polyphosphate, calcium oxyapatite, sodium carbonate, sodium bicarbonate, and combinations thereof. If a silica, preferably the silica is a precipitated silica (e.g., sodium silicate solution by destabilizing with acid as to yield very fine particles) such as those from the ZEODENT® series from Huber Engineered Materials (e.g., ZEODENT® 103, 124, 113 115, 163, 165, 167). It is acknowledged that some of these silicas (e.g., synthetic amorphous silica) can perform both abrasive and thickening functions, but are included herein under the term "abrasive" for purposes of the present invention. Preferably the oral care composition comprises from 1% to 35%, more preferably from 5% to 25% of abrasive, by weight of the composition.

Flavoring Agent

The oral care composition herein may include from 0.01% to 5%, preferably from 0.1% to 2%, by weight of the composition, of a flavoring agent. Examples of suitable flavoring agent that may be used in the oral care composition include those described in U.S. Pat. No. 8,691,190; Haught, J. C., from column 7, line 61 to column 8, line 21. In some examples, the flavoring agent may be selected from methyl salicylcate, menthol, eugenol and cineol. In some examples, the oral care composition may comprise a flavor mixture which is free of or substantially free of methyl salicylcate, menthol, eugenol and cineol.

Sweetener

The oral care compositions herein may include a sweetening agent. The sweetening agent is generally present in the oral care compositions at levels of from 0.005% to 5%, by weight of the composition. Suitable examples of sweetener include saccharin, dextrose, sucrose, lactose, xylitol, maltose, levulose, aspartame, sodium cyclamate, D-tryptophan, dihydrochalcones, acesulfame, sucralose, neotame, and mixtures thereof. Other suitable examples of sweetener are described in U.S. Pat. No. 8,691,190; Haught, J. C. from column 9, line 18 to column 10, line 18.

Coloring Agents

The oral care compositions herein may include a coloring agent present in the amount of from 0.001% to 0.01%, by weight of the compositions. The coloring agent may be in the form of an aqueous solution, preferably 1% coloring agent in a solution of water. Suitable examples of coloring agents may include pigments, pealing agents, filler powders, talc, mica, magnesium carbonate, calcium carbonate, bismuth oxychloride, zinc oxide, and other materials capable of creating a visual change to the oral care compositions. Other suitable examples may include titanium dioxide ($TiO_2$). Titanium dioxide is a white powder which adds opacity to the compositions and is generally present in the oral care compositions at levels of from 0.25% to 5%, by weight of the composition.

Other Ingredients

The present oral care composition can comprise the usual and conventional ancillary components that are known to one skilled in the art. Optional ingredients include, for example, but are not limited to, anti-plaque agent, anti-sensitivity agent, whitening and oxidizing agent, anti-inflammatory agent, anti-calculus agent, chelating agent, tooth substantive agent, analgesic and anesthetic agent. It will be appreciated that selected components for the oral care compositions must be chemically and physically compatible with one another.

Method of Use

In one aspect, the present invention relates to a method for cleaning or polishing teeth in a human subject. The method of cleaning or polishing herein comprises contacting a subject's teeth with the oral care compositions according to the present invention.

In another aspect, the present invention also relates to a method of promoting Gum Health in a human subject comprising administering to the subject's oral cavity an oral care composition according to the present invention, wherein preferably the administering occurs at least once a day, more preferably at least twice a day.

In yet another aspect, the present invention relates to a use of amino acid for making an oral care composition containing stannous, especially containing no zinc, for promoting Gum Health in a human subject. Preferably, the method of promoting Gum Health occurs at least within a period selected from the group consisting of:
  a) from time 0 hours to 72 hours;
  b) from time 0 hours to 48 hours;
  c) from time 0 hours to 24 hours;
    wherein time 0 hour is the time when the oral care composition according to the present invention is administrated.

In yet another aspect, the present invention also relates to a method of promoting Gum Health, wherein promoting Gum Health comprises:
  (i) improving gingival wound healing in the oral cavity; and
  (ii) improve reduction of bacterial activity in the oral cavity.

The methods as described above may be by brushing (e.g., toothbrushing) with an oral care composition (e.g., dentifrice) or rinsing with an oral care composition (e.g., dentifrice slurry or mouth rinse). The oral care compositions may be applied neat or via a delivery apparatus such as, for example, a toothbrush. Other methods include contacting the topical oral gel, mouth spray, toothpaste, dentifrice, tooth gel, tooth powders, tablets, subgingival gel, foam, mouse, chewing gum, lipstick, sponge, floss, petrolatum gel, or denture product or other form with the subject's teeth and oral mucosa. Depending on the embodiment, the oral care composition may be used as frequently as toothpaste, or may be used less often, for example, weekly, or used by a professional in the form of a prophy paste or other intensive treatment.

EXAMPLES

The following examples and descriptions further clarify embodiments within the scope of the present invention. These examples are given solely for the purpose of illustration and are not to be construed as limitations of the present invention as many variations thereof are possible without departing from the spirit and scope.

Example A: Examples 1 to 17

Examples 1 to 17 are dentifrice compositions shown below with amounts of components in wt %. They may be suitably prepared by conventional methods chosen by the formulator. Examples 1-8 are inventive formulations according to the present invention, made with a stannous ion source (e.g., stannous chloride) and a single amino acid (e.g., arginine, citrulline, glutamine or glutamic acid), without present of zinc ion source respectively. In parallel, comparative formulations examples 9-17, are prepared. Examples 9-16 are made with stannous, a single amino acid, as well as zinc ion source (zinc citrate) at two concentrations, while control Example 17 is made without the amino acid or the zinc ion source. All of the compositions are prepared by admixture of the components in Tables 1 and 2, in the proportions indicated.

TABLE 1

Inventive Compositions Examples 1 to 8

| Ingredients | Amount (Wt %) | | | | | | | |
|---|---|---|---|---|---|---|---|---|
| | Ex. 1 | Ex. 2 | Ex. 3 | Ex. 4 | Ex. 5 | Ex. 6 | Ex. 7 | Ex. 8 |
| Sorbitol Solution 70% (Archer Daniels Midland) | 48.000 | 48.000 | 48.000 | 48.000 | — | — | — | — |
| Sodium Fluoride | 0.321 | 0.321 | 0.321 | 0.321 | — | — | — | — |
| Arginine | 2.00 | — | — | — | 2.00 | — | — | — |
| Citrulline | — | 2.00 | — | — | — | 2.00 | — | — |
| Glutamine | — | — | 2.00 | — | — | — | 2.00 | — |
| Glutamic Acid | — | — | — | 2.00 | — | — | — | 2.00 |
| Glycerin | — | — | — | — | 35.500 | 35.500 | 35.500 | 35.500 |
| Propylene Glycol | — | — | — | — | 7.000 | 7.000 | 7.000 | 7.000 |
| PEG-6 | — | — | — | — | 7.000 | 7.000 | 7.000 | 7.000 |
| Sodium Polyphosphate | — | — | — | — | 13.000 | 13.000 | 13.000 | 13.000 |
| Trosodium Phosphate Dodecahydrate | — | — | — | — | 1.100 | 1.100 | 1.100 | 1.100 |
| Stannous Fluoride | — | — | — | — | 0.454 | 0.454 | 0.454 | 0.454 |
| Zinc Lactate Dihydrate | — | — | — | — | — | — | — | — |
| Zinc Citrate | — | — | — | — | — | — | — | — |
| Stannous Chloride Dihydrate | 1.160 | 1.160 | 1.160 | 1.160 | 0.462 | 0.462 | 0.462 | 0.462 |
| Sodium Gluconate | 1.064 | 1.064 | 1.064 | 1.064 | 1.099 | 1.099 | 1.099 | 1.099 |
| Xanthan Gum | 0.875 | 0.875 | 0.875 | 0.875 | 0.250 | 0.250 | 0.250 | 0.250 |
| Carrageenan Mixture Iota Silica | 1.500 | 1.500 | 1.500 | 1.500 | 0.600 | 0.600 | 0.600 | 0.600 |
| Silica Abrasive | 16.000 | 16.000 | 16.000 | 16.000 | 25.000 | 25.000 | 25.000 | 25.000 |
| Thickening Silica | — | — | — | — | 0.750 | 0.750 | 0.750 | 0.750 |
| Sodium Lauryl Sulfate (28% soln.) | 7.500 | 7.500 | 7.500 | 7.500 | 7.500 | 7.500 | 7.500 | 7.500 |
| Sodium Saccharin | 0.300 | 0.250 | 0.300 | 0.300 | 0.700 | 0.700 | 0.700 | 0.700 |
| Flavor/sensate oils | 1.100 | 1.100 | 1.100 | 1.100 | 1.200 | 1.200 | 1.200 | 1.200 |
| Sodium Hydroxide | 0.980 | 0.980 | 0.980 | 0.980 | — | — | — | — |
| Water and minors (e.g., color soln.) | q.s. | q.s. | q.s. | q.s. | q.s. | qs | q.s. | q.s. |
| Total | 100% | 100% | 100% | 100% | 100% | 100% | 100% | 100% |
| Target pH | 6.5 | 6.5 | 6.5 | 6.5 | 6.5 | 6.5 | 6.5 | 6.5 |

TABLE 2

Comparative Compositions Examples 9 to 17

| Ingredients | Amount (Wt %) | | | | | | | | |
|---|---|---|---|---|---|---|---|---|---|
| | Ex. 9 | Ex. 10 | Ex. 11 | Ex. 12 | Ex. 13 | Ex. 14 | Ex. 15 | Ex. 16 | Ex. 17 |
| Sorbitol Solution 70% (Archer Daniels Midland) | 48.000 | 48.000 | 48.000 | 48.000 | 48.000 | 48.000 | 48.000 | 48.000 | 48.000 |
| Sodium Fluoride | 0.321 | 0.321 | 0.321 | 0.321 | 0.321 | 0.321 | 0.321 | 0.321 | 0.321 |
| Arginine | 2.00 | — | — | — | 2.00 | — | — | — | — |
| Citrulline | — | 2.00 | — | — | — | 2.00 | — | — | — |
| Glutamine | — | — | 2.00 | — | — | — | 2.00 | — | — |

TABLE 2-continued

Comparative Compositions Examples 9 to 17

| Ingredients | Ex. 9 | Ex. 10 | Ex. 11 | Ex. 12 | Ex. 13 | Ex. 14 | Ex. 15 | Ex. 16 | Ex. 17 |
|---|---|---|---|---|---|---|---|---|---|
| Glutamic Acid | — | — | — | 2.00 | — | — | — | 2.00 | — |
| Zinc Citrate | 0.533 | 0.533 | 0.533 | 0.533 | 1.066 | 1.066 | 1.066 | 1.066 | — |
| Stannous Chloride Dihydrate | 1.160 | 1.160 | 1.160 | 1.160 | 1.160 | 1.160 | 1.160 | 1.160 | 1.160 |
| Sodium Gluconate | 1.064 | 1.064 | 1.064 | 1.064 | 1.064 | 1.064 | 1.064 | 1.064 | 1.064 |
| Xanthan Gum | 0.875 | 0.875 | 0.875 | 0.875 | 0.875 | 0.875 | 0.875 | 0.875 | 0.875 |
| Carrageenan Mixture Iota Silica | 1.500 | 1.500 | 1.500 | 1.500 | 1.500 | 1.500 | 1.500 | 1.500 | 1.500 |
| Silica Abrasive | 16.000 | 16.000 | 16.000 | 16.000 | 16.000 | 16.000 | 16.000 | 16.000 | 16.000 |
| Thickening Silica | — | — | — | — | — | — | — | — | — |
| Sodium Lauryl Sulfate (28% soln.) | 7.500 | 7.500 | 7.500 | 7.500 | 7.500 | 7.500 | 7.500 | 7.500 | 7.500 |
| Sodium Saccharin | 0.300 | 0.250 | 0.300 | 0.300 | 0.300 | 0.250 | 0.300 | 0.300 | 0.300 |
| Flavor/sensate oils | 1.100 | 1.100 | 1.100 | 1.100 | 1.100 | 1.100 | 1.100 | 1.100 | 1.100 |
| Sodium Hydroxide | 0.980 | 0.980 | 0.980 | 0.980 | 0.980 | 0.980 | 0.980 | 0.980 | 0.980 |
| Water and minors (e.g., color soln.) | q.s. | q.s. | q.s. | q.s. | q.s. | q.s. | q.s. | q.s. | q.s. |
| Total | 100% | 100% | 100% | 100% | 100% | 100% | 100% | 100% | 100% |
| Target pH | 6.5 | 6.5 | 6.5 | 6.5 | 6.5 | 6.5 | 6.5 | 6.5 | 6.5 |

Example B—Assay for Measuring Improve Endotoxin Neutralization of Anti-Bacterial Agent in the Biofilms In order to determine improved endotoxin neutralization of anti-bacterial agent in the biofilms, the following assay is used to assess LPS binding efficiency of stannous ions via measurement of a fluorescent dye that is bound to lipid A of LPS in in situ plaque biofilms for inventive oral care compositions of the present invention and controls. Details of the assay are described below.

(a) Substrate for Biofilm Growth

Hydroxyapatite ("HA") disks are used for in situ growth of biofilms. The HA disks are designed having three parallel grooves (i.e., 200 µm wide; 200 µm deep for two sides' grooves; while 500 µm wide and 500 µm deep for the middle groove) in each disk. When attaching disks to subject's mouth, keep these grooves vertical, to mimic interproximal gap between teeth, which is the hard-to-clean area where plaque generally tends to accumulate. This model allows the collection of undisturbed plaque from the grooves. HA disks are manufactured by Shanghai Bei'erkang biomedicine limited company.

(b) Wearing the Splint

Human subjects wear the splint. Each subject wears up to 12 HA disks on the splint to ensure that, at least, 9 HA disks are available after 48 hours. A non-limiting example of such a splint and HA disks are shown in FIG. 1. With reference to FIG. 1, the device (1) holds a plurality of HA disks (2a-2d). In a specific example, and with reference to FIG. 2, the HA disk (201) has three parallel grooves (203) (the two sides' grooves (203a and 203c) are 300 µm wide and 300 µm deep; while the middle grove (203b) (in between the two side grooves) is 500 µm wide and 500 µm deep). The middle groove is designed wider and deeper than the two sides' grooves so that the HA disk can be more easily separated into two identical half-disks for head-to-head comparison purposes. FIG. 3 is a schematic of a cross-sectional view of the groove (2003) with biofilm (2005) therein. Further details of the HA disks are described in US2017/0056531 (e.g. paragraphs [0019]-[0020]).

Although not shown in FIG. 3, the disks can be positioned such that the recede is in the inter-dental space between the teeth (since this location is prone to plaque (given the difficulty in cleaning, etc.)). The subjects withdraw the splint only during meals (the splint stored in an opaque container in humid conditions) and to perform oral hygiene procedures Immediately thereafter, the splint is worn again. Subjects are asked to use a straw when drinking.

(c) In-Situ Biofilms Release from HA Desk

All HA disks are removed from the splint at 48 hours by tweezers. Tweezers are used to hold the edge of HA chips and transfer the HA disk to a 2 mL centrifuge tube containing phosphate buffered saline (PBS) solution. Tweezers are washed thoroughly (water; 75% alcohol; and then deionized water) before every disk transfer.

(d) Preparation of Toothpaste Supernatant 15 grams of deionized water is added to 5 grams toothpaste (using any one of the inventive Composition Examples 1-8, Comparative Composition Examples 9-17. After stirring thoroughly, the mixture is centrifuge at 12,000 RPM for 20 minutes. The supernatant is prepared one day before usage and stored at 4° C.

(e) Confocal Laser Scanning Microscopy

After the HA disks are removed from the splint. The HA disks are used for ex vivo treatment by the different inventive and control compositions. After being treated with the subject supernatant and labeled with microbial fluorescent probe and stannous fluorescent probe (such as described in PCT Publication No. WO2015/139263; Shi et al.), the biofilms in the grooves are measured by confocal laser scanning microscopy ("CLSM") (as described below). Preferably, the neutralized-LPS fluorescent probe is BODIPY-TR-cadaverine (BC) (available from Thermo Fisher). Preferably, the microbial fluorescent probe is the Molecular Probes™ LIVE/DEAD® BacLight™ system (available from Thermo Fisher).

(f) Disk Preparation

The HA disks are rinsed in PBS solution and each HA disk is divided into two halves by tweezers. Thereafter, each half-disk is placed into 500-1000 μL of PBS solution statically for 1 minute. Each disk is treated for two minutes by either PBS solution or toothpaste supernatant. Each disk is washed by holding each disk with tweezers, shaken for ten rounds of back and forth in 1 mL of PBS solution, and then this washing cycle is repeated. Then each disk is immersed into 500-1000 μL PBS solution statically for 5 minutes.

(g) Fluorescence Staining and Microscopy

The LPS neutralization effect was evaluated using BODIPY-TR-cadaverine (BC), a fluorescent dye that is bound to lipid A, thereby suppressing its fluorescence. BC is displaced by agents with an affinity for this lipid. When LPS are bound by other ions, e.g., stannous, BC is released from the LPS and its fluorescence is proportional to the amount of free (unbound) BC present. Therefore, the level of fluorescence indicates the amount of neutralized (bound) LPS versus free (unbound) LPS, and the efficacy of an antibacterial agent in reducing the biofilm's toxicity. The greater the amount of bound LPS, the lower its toxicity.

After treatment and immersing, each half-disk is stained with the BODIPY-TR-cadaverine (BC) probe together with Syto-9 probe (containing 5 μM BC probe and 5 μM Sn probe) for 30 minutes in the dark. After staining, each disk is immersed into 500-1000 μL PBS solution statically for 2 minutes. The disks are washed again, by holding each disk with tweezers, shaken for five rounds of back and forth in 1 mL PBS solution, and repeated. For SYTO-9/BC dye stained samples, the following parameters are used: λex=488 nm/543 nm, λem=500/580 nm, 20× objective lens, and scanning from bottom of surface bacteria for 60 μm with step size=3 μm.

(h) Confocal Laser Scanning Microscopy

The Leica™ TCS SP8 AOBS spectral confocal microscope is used. The confocal system consists of a Leica™ DM6000B upright microscope and a Leica™ DMIRE2 inverted microscope. An upright stand is used for applications involving slide-mounted specimens; whereas the inverted stand, having a 37° C. incubation chamber and $CO_2$ enrichment accessories, provides for live cell applications. The microscopes share an exchangeable laser scan head and, in addition to their own electromotor-driven stages, a galvanometer-driven high precision Z-stage which facilitates rapid imaging in the focal (Z) plane. In addition to epifluorescence, the microscopes support a variety of transmitted light contrast methods including bright field, polarizing light and differential interference contrast, and are equipped with 5×, 20×, 40×, 63× (oil and dry) and 100× (oil) Leica™ objective lenses.

The laser scanning and detection system is described. The TCS SP8 AOBS confocal system is supplied with four lasers (one diode, one argon, and two helium neon lasers) thus allowing excitation of a broad range of fluorochromes within the UV, visible and far red ranges of the electromagnetic spectrum. The design of the laser scan head, which incorporates acousto-optical tunable filters ("AOTF"), an acousto-optical beam splitter ("AOBS") and four prism spectrophotometer detectors, permits simultaneous excitation and detection of three fluorochromes. The upright microscope also has a transmission light detector making it possible to overlay a transmitted light image upon a fluorescence recording.

Leica™ Confocal software is used. The confocal is controlled via a standard Pentium PC equipped with dual monitors and running Leica™ Confocal Software. The Leica Confocal Software provides an interface for multi-dimensional image series acquisition, processing and analysis, that includes 3D reconstruction and measurement, physiological recording and analysis, time-lapse, fluorochrome co-localization, photo-bleaching techniques such as FRAP and FRET, spectral immixing and multicolour restoration. Regarding image analysis, the SYTO-9/BC probe stained samples are chosen to quantify fluorescence intensity of red and green pixels. Using the software, the fluorescence intensity ratio (FIR) of bound LPS/bacterial cell was calculated. This ratio of fluorescence intensity indicates the relative amount of bound (neutralized) LPS per unit of bacteria, and the efficacy of an agent in reducing the biofilm's toxicity. The greater the fluorescence intensity ratio, the higher LPS endotoxin neutralization efficacy.

Results: Subjects are treated with the Inventive Composition Ex. 1-4 (i.e., Sn+2.00% Amino Acid without Zinc), Comparative Composition Ex. 9-16 (i.e., Sn+2.00% Amino Acid with Zinc), Comparative Composition Ex. 17 (i.e., Sn without amino acid nor Zinc), and the PBS as negative control. The results are provided in Table 3.

TABLE 3

Endotoxin neutralization in Biofilm

| | Fluorescence intensity ratio (FIR) of bound LPS/bacterial cell |
|---|---|
| Inventive Composition Ex. 1 | 0.73 |
| Inventive Composition Ex. 2 | 0.79 |
| Inventive Composition Ex. 3 | 0.8 |
| Inventive Composition Ex. 4 | 0.83 |
| Comparative Composition Ex. 9 | 0.64 |
| Comparative Composition Ex. 10 | 0.66 |
| Comparative Composition Ex. 11 | 0.68 |
| Comparative Composition Ex. 12 | 0.69 |
| Comparative Composition Ex. 13 | 0.6 |
| Comparative Composition Ex. 14 | 0.64 |
| Comparative Composition Ex. 15 | 0.64 |
| Comparative Composition Ex. 16 | 0.65 |
| Comparative Composition Ex. 17 | 0.63 |
| Control (PBS) | 0 |

The results demonstrate the markedly higher Fluorescence intensity ratio (FIR) of bound LPS/bacterial cell with the Inventive Composition Ex. 1 (0.73), Inventive Composition Ex. 2 (0.79), Inventive Composition Ex. 3 (0.8), Inventive Composition Ex. 4 (0.83) over the Comparative Composition Ex. 9-17 (0.6-0.69) and the Control PBS(0). In effect this data supports the improved endotoxin neutralization of the stannous ion in the biofilms when combined with an amino acid (e.g., arginine, citrulline, glutamine and glutamic acid) and free of Zn over the control with an amino acid (e.g., arginine, citrulline, glutamine and glutamic acid) and Zn salts. Further comparing Inventive Composition Ex.

1 to 4 with Comparative Composition Ex. 17, the data show improved endotoxin neutralization of the stannous ion in the biofilms when combined with an amino acid vs. only stannous ion without amino acid (0.73-0.83 vs. 0.63).

Example C—Assay for Measuring Improved Wound Healing of Human Gingival Fibroblasts In-vitro human gingival fibroblasts are used to assess the effects of wound healing migration as a result of treatment with Inventive Compositions and Comparative Compositions. The method involves three stages:

Stage 1—Culturing Primary Human Gingival Fibroblasts ("HGF")

Human gingival fibroblasts are collected from tooth extraction patients and washed with 5 mL of PBS (phosphate buffered saline). The tissues are chopped into small pieces and placed into 15 mL centrifuge tube. The samples are digested with equal amounts of 1 mL 8% dispase and 1 mL 6% collagenase for 1 hr at 37° C., during which time the samples need to be shaken every 15 minutes. Once the digestion process is complete, the tube is centrifuged at 1100 RPM for 6 minutes at room temperature. After centrifugation, a pellet of cells is formed in the bottom of the tube separating them from the supernatant solution. Then the supernatant is discarded and the cell pellet is suspended in 3 mL of fresh Minimum Essential Medium ("MEM", available from Thermo Fisher) culture media then transferred to a petri dish. The petri dish with cells are placed in the incubator at 37° C. with 5% $CO_2$ for about 10 days. The petri dish is checked for changes in media color every two days. Fresh culture media is replaced if changes in media color occurred.

Stage 2—Sub-Culturing Human Gingival Fibroblast

When there is 80-90% cell monolayer coverage of the petri dish, then the present culture media is removed and washed with 5 mL of PBS. 1 mL 0.25% trypsin-EDTA solution is added and the cells sit for about 1-2 minutes at 37° C. until the cells are visibly round-shaped. It may be necessary to tap the petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 4 mL of fresh MEM culture media in the same centrifuge tube. 4 petri dishes are each placed with 1 mL cell suspension and 9 mL fresh MEM culture media in the incubator at 37° C. with 5% $CO_2$ for about 3-5 days until 80-90% cell monolayer coverage on the petri dishes are observed. This stage should be repeated 2-4 times before the wound healing assay to achieve the highest cell viability.

Stage 3—Wound Healing Assay

When there is 80-90% cell monolayer coverage on the petri dishes, the present culture media is removed and washed with 5 mL of PBS. 1 mL 0.25% trypsin-EDTA solution is added and the cells sit for about 1-2 minute at 37° C. until the cells are visibly round-shaped. It may be necessary to tap the culture petri dish to remove any sticky cells from the petri dish surface. At least 1 mL of fresh MEM culture media is added to inactivate the trypsin and the cells are collected into a 15 mL centrifuge tube. The tube is then centrifuged at 1100 RPM for 6 minutes at room temperature. The supernatant is discarded and cell pellet is re-suspended in 6 mL of fresh MEM culture media. 1 mL cell suspension and 1 mL fresh MEM culture media are respectively added into each well of a 6-well plate. The plates are incubated at 37° C. with 5% $CO_2$ until 50-70% cell monolayer coverage is formed. The outer bottoms of wells are then marked with a line in middle as the reference line during image acquisition. A wound is created manually by scraping the right half of cell monolayer with a sterilized 1 mL pipette tip. The cells are washed with 2 mL PBS to remove any suspended cells until no suspended cells are visible. 2 mL culture media, and 2 ml culture media containing 1% Comparative Compositions or 2 mL culture media containing 1% Inventive Compositions are added to the wells.

High density digital images of the HGF are captured with an Olympus® IX71 digital SLR camera with an Olympus® UIS2 WHN10× objective lens. The first images are acquired at time 0 hr (i.e., Baseline) by using the middle line markings on the plates as a reference line. The plates are then incubated at 37° C. with 5% $CO_2$ for varying time intervals as described below. The matched photographed region is acquired as previously, and images are acquired at later time intervals (e.g., 24 hrs, 48 hr, 72 hrs, etc.) after baseline to assess the cell coverage (%) as an indication of the wound healing performance under the different treatment legs Images are evaluated by Wimasis® WimScratch software (available from Wimasis GmbH, Germany) to determine the degree (i.e., percentage) of HGF cell coverage (i.e., wound healing) pass the marked wound boundary, as compared to the matching baseline image for each sample. WimScratch software utilizes advanced edge detection and overlay techniques to recognize cells and blank area, i.e. the green overlay in the image represents the cell-covered area of the particular image and the grey area represents the wound area. The readout is presented for both area and is normalized as percent of total area.

Results: With reference to Table 4, the results show that the Inventive Composition Ex. 1 containing Arginine and Ex. 2 containing Citrulline effectively improve the wound healing though increased cell coverage (i.e. 8.70%=58.70% total coverage–50.00% baseline) post the marked wound relative to the lower cell coverage (6.40%=56.40% total coverage–50.00% baseline) for the HGF treated with the Comparative Composition Ex. 17 without amino acid and Zinc.

TABLE 4

Wound Healing Increase 24 hrs, 48 hrs, 72 hrs Post-Treatment

|  | 24 h | 72 h |
| --- | --- | --- |
| Inventive Composition Ex. 1 | 8.70% | 28.30% |
| Inventive Composition Ex. 2 | 16.70% | 37.80% |
| Comparative Composition Ex. 17 | 6.40% | 22.80% |

Example D—Mouth Rinse Compositions

Mouth rinse compositions according to the present invention are shown below as Examples 18-20 in Table 5. These compositions contain a stannous ion source and an amino acid without presence of zinc. Preferably, these compositions exhibit improve Gum Health benefits versus commercially available formulations without these ingredients.

TABLE 5

Mouth Rinse Formulations

| Ingredients | Amount (Wt %) | | |
|---|---|---|---|
| | Ex. 18 | Ex. 19 | Ex. 20 |
| Glycerin | 5.000 | 5.000 | 5.000 |
| Stannous Chloride Dihydrate | 0.116 | 0.116 | 0.116 |
| Arginine | 0.050 | 0.500 | 2.00 |
| Sucralose | 0.030 | 0.030 | 0.030 |
| Ethanol | 5.000 | 5.000 | 5.000 |
| Methyl Paraben | 0.020 | 0.020 | 0.020 |
| Propyl Paraben | 0.005 | 0.005 | 0.005 |
| Flavor/sensate oils | 0.100 | 0.100 | 0.100 |
| Performathox 490 | 0.050 | 0.050 | 0.050 |
| Water | q.s. | q.s. | q.s. |
| Total | 100% | 100% | 100% |
| Target pH | 6 | 6 | 6 |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm."

Every document cited herein, including any cross referenced or related patent or application and any patent application or patent to which this application claims priority or benefit thereof, is hereby incorporated herein by reference in its entirety unless expressly excluded or otherwise limited. The citation of any document is not an admission that it is prior art with respect to any invention disclosed or claimed herein or that it alone, or in any combination with any other reference or references, teaches, suggests or discloses any such invention. Further, to the extent that any meaning or definition of a term in this document conflicts with any meaning or definition of the same term in a document incorporated by reference, the meaning or definition assigned to that term in this document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. An oral care composition comprising:
   (a) stannous fluoride;
   (b) stannous chloride; and
   (c) amino acid,
wherein the oral care composition is substantially free of a zinc ion source and a polyphosphate.

2. The oral care composition of claim 1, wherein the amino acid comprises a basic amino acid, a neutral amino acid, an acidic amino acid, or combinations thereof.

3. The oral care composition of claim 2, wherein the amino acid comprises arginine, lysine, serine, histidine, ornithine, alanine, aminobutyrate, asparagine, citrulline, cysteine, cystine, glutamine, glycine, hydroxyproline, isoleucine, leucine, methionine, phenylalanine, proline, serine, taurine, threonine, tryptophan, tyrosine, valine, aspartic acid, glutamic acid; or combinations thereof.

4. The oral care composition of claim 1, wherein the composition comprises from 0.01% to 5%, by weight of the composition, of a thickening agent selected from a thickening polymer, a thickening silica, or a combination thereof.

5. The oral care composition of claim 1, wherein the composition comprises from 1% to 60%, by weight of the composition, of a humectant.

6. The oral care composition of claim 5, wherein the humectant comprises glycerin, sorbitol, or combinations thereof.

7. The oral care composition of claim 1, wherein the composition has a pH of 9.0 or less.

8. The oral care composition of claim 1, wherein the composition comprises abrasive.

9. The oral care composition of claim 8, wherein the abrasive comprises silica abrasive, calcium-containing abrasive or combinations thereof.

10. The oral care composition of claim 9, wherein the silica abrasive comprises precipitated silica.

11. The oral care composition of claim 9, wherein the calcium-containing abrasive comprises calcium carbonate, dicalcium phosphate, tricalcium phosphate, calcium orthophosphate, calcium metaphosphate, calcium polyphosphate, calcium oxyapatite, sodium carbonate, sodium bicarbonate, or combinations thereof.

12. An oral care composition comprising:
   (a) anti-caries agent;
   (b) stannous chloride; and
   (c) amino acid,
wherein the oral care composition is substantially free of a zinc ion source and a polyphosphate.

13. The oral care composition of claim 12, wherein the anti-caries agent comprises stannous fluoride, sodium fluoride, potassium fluoride, sodium monofluorophosphate, indium fluoride, amine fluoride, zinc fluoride, or combinations thereof.

14. The oral care composition of claim 13, wherein the anti-caries agent is selected from the group consisting of sodium fluoride, sodium monofluorophosphate, amine fluoride, or combinations thereof.

15. The oral care composition of claim 14, wherein the amino acid comprises a basic amino acid, a neutral amino acid, an acidic amino acid, or combinations thereof.

16. The oral care composition of claim 15, wherein the amino acid comprises arginine, lysine, serine, histidine, ornithine, alanine, aminobutyrate, asparagine, citrulline, cysteine, cystine, glutamine, glycine, hydroxyproline, isoleucine, leucine, methionine, phenylalanine, proline, serine, taurine, threonine, tryptophan, tyrosine, valine, aspartic acid, glutamic acid; or combinations thereof.

17. The oral care composition of claim 14, wherein the composition comprises from 0.01% to 5%, by weight of the composition, of a thickening agent selected from a thickening polymer, a thickening silica, or a combination thereof.

18. The oral care composition of claim 14, wherein the composition comprises from 1% to 60%, by weight of the composition, of a humectant.

19. The oral care composition of claim 18, wherein the humectant comprises glycerin, sorbitol, or combinations thereof.

20. The oral care composition of claim 14, wherein the composition has a pH of 9.0 or less.

21. The oral care composition of claim 14, wherein the composition comprises abrasive.

22. The oral care composition of claim 21, wherein the abrasive comprises silica abrasive, calcium-containing abrasive or combinations thereof.

23. The oral care composition of claim 22, wherein the silica abrasive comprises precipitated silica.

24. The oral care composition of claim 22, wherein the calcium-containing abrasive comprises calcium carbonate, dicalcium phosphate, tricalcium phosphate, calcium orthophosphate, calcium metaphosphate, calcium polyphosphate, calcium oxyapatite, sodium carbonate, sodium bicarbonate, or combinations thereof.

* * * * *